US00PP24079P3

(12) United States Plant Patent
Hurd

(10) Patent No.: US PP24,079 P3
(45) Date of Patent: Dec. 10, 2013

(54) ***HIBISCUS* PLANT NAMED 'MIDNIGHT MARVEL'**

(50) Latin Name: ***Hibiscus* hybrid (L.)**
Varietal Denomination: Midnight Marvel

(75) Inventor: Kevin A. Hurd, Chicago, IL (US)

(73) Assignee: Walters Gardens Inc, Zeeland, MI (US)

( * ) Notice: Subject to any disclaimer, the term of this patent is extended or adjusted under 35 U.S.C. 154(b) by 92 days.

(21) Appl. No.: 13/385,989

(22) Filed: Mar. 19, 2012

(65) Prior Publication Data

US 2013/0247260 P1 Sep. 19, 2013

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter-hardy herbaceous *Hibiscus* hybrid plant named 'Midnight Marvel' comprising a naturally-short, compact, heavy-branching habit. The foliage has strong dark purple overtones, and the plant flowers with a multitude of deep scarlet-red flowers with a darker red eye over at least 12 weeks during the summer until frost.

1 Drawing Sheet

Botanical classification: *Hibiscus* hybrid (L.).
Variety denomination: 'Midnight Marvel'.

BACKGROUND AND ORIGIN OF THE PLANT

The present invention relates to the new and distinct hardy, herbaceous, *hibiscus* plant, *Hibiscus* 'Midnight Marvel' hybridized by Kevin A. Hurd in the summer of 2008 at a nursery in Zeeland, Mich. The new plant, originally labeled # 07-314-10, is from a cross between *Hibiscus* 'Summer Storm' U.S. Plant Pat. No. 20,443 (female pod parent) times the proprietary hybrid # 06-87-02 (not patented) (male pollen parent). Both parents have a complex mixture of species in them, most likely including the species: *moscheutos, coccineus* and *laevis* (formerly *militaris*). *Hibiscus* 'Midnight Marvel' was first asexually propagated in 2009 by both stem cuttings and sterile tissue culture at the same nursery in Zeeland, Mich. The resultant plants have been found to be stable and true to type in successive generations of asexual reproduction.

BRIEF SUMMARY OF THE PLANT

*Hibiscus* 'Midnight Marvel' differs from its parents as well as all other hardy *hibiscus* known to the applicant in many traits. The foliage color of 'Midnight Marvel' is a dark green with an overlay of grayed purple and the foliage shape of 'Midnight Marvel' is variable, depending on the time of year and position on the stem. Most leaves are palmatifid or palmately lobed to cleft with some either young leaves or those on immature plants being palmately ovate. The flowers of 'Midnight Marvel' are nearly flat-faced with deep scarlet-red petals. The most similar *hibiscus* to 'Midnight Marvel' known to the applicant are *Hibiscus* 'Cranberry Crush' U.S. Plant Pat. No. 21,984, *Hibiscus* 'Summer Storm' U.S. Plant Pat. No. 20,443, *Hibiscus* 'Fireball' U.S. Plant Pat. No. 13,631 and *Hibiscus* 'Kopper King' U.S. Plant Pat. No. 10,793. Compared to 'Cranberry Crush' the new plant has a flatter flower with deeper scarlet-red flower color, not as lustrous petals, and the foliage is much darker purple. Compared to 'Summer Storm' and 'Kopper King' the new plant has a much more intense scarlet-red flower, is shorter in habit and finer in leaf than 'Kopper King'. Compared to 'Fireball' the new plant is shorter, more compact and less splaying in habit with much darker purple foliage. Compared to the male parent, # 06-87-02, the new plant is shorter, more compact and better branched with a richer deep scarlet-red flower.

*Hibiscus* 'Midnight Marvel' is a unique hardy herbaceous *hibiscus* with the following combined traits:

1. Hardy perennial, naturally short, rounded habit with dense branching.
2. Many slightly cupped flowers over a prolonged season having deep scarlet-red overlapping petals and a darker red lustrous eye.
3. Variably shaped foliage of dark green with strong dark purple overlay.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
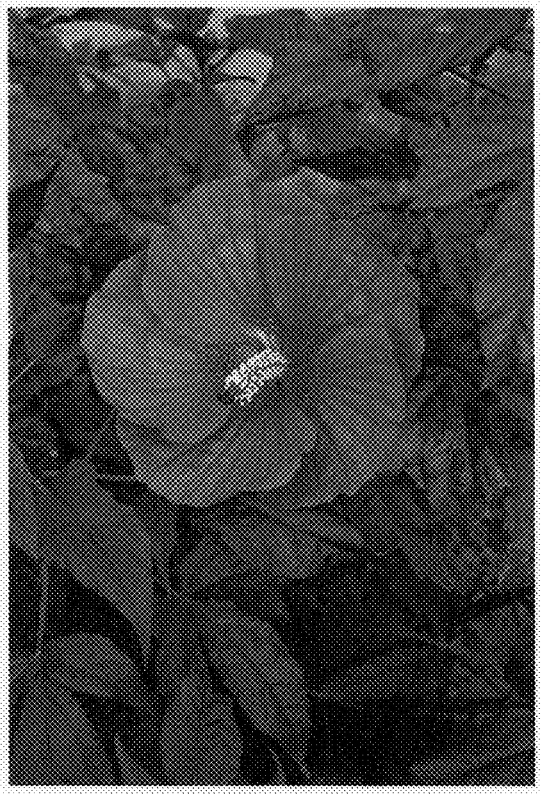
FIG. 1 shows a close-up of the flower with grayed-purple overlay on dark green foliage.
Figure 2:
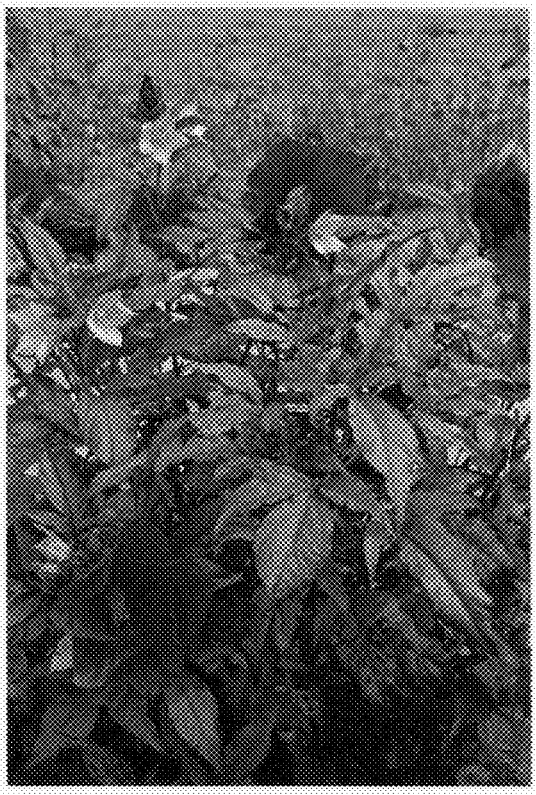
FIG. 2 shows the plant short, compact, rounded habit of a three year-old plant.

The following descriptions and color references are based on the 2001 edition of The Royal Horticultural Society Colour Chart except where common dictionary terms are used. The new plant, *Hibiscus* 'Midnight Marvel', has not been observed under all possible environments. The phenotype may vary slightly with different environmental conditions, such as temperature, light, fertility, moisture and maturity levels, but without any change in the genotype. The following observations and size descriptions are of one year-old plants in the loamy-sand open field trials of a nursery in Zeeland, Mich. with supplemental fertilizer and water as needed. The plants are natural habit and were not treated with plant growth regulators, nor were they pinched at any time in the growth year.

Parentage: *Hibiscus* 'Summer Storm' U.S. Plant Pat. No. 20,443 (female pod parent) times the proprietary hybrid # 06-87-02 (not patented) (male pollen parent).

Propagation:

*Method.*—Stem cuttings and sterile plant tissue culture division.

*Time to initiate roots from tissue culture.*—About two weeks.

*Rooting habit.*—Normal, branching, developing thick to about 3.0 cm diameter, fleshy; root color creamy white between RHS 159A and lighter than RHS 159 D depending on soil type.

*Crop time.*—Under normal summer growing conditions 12 to 16 weeks to flower in a four-liter container from cutting. Plant vigor is very good.

Plant description:

*Plant shape and habit.*—Hardy herbaceous perennial with 2 to 4 thick upright and heavily branched main stems producing a rounded mound about 85.0 cm tall and 80.0 cm wide; 8 to 15 primary branches per main stem protruding at 60° to 75° angle from horizontal, secondary branches on the lower one third to half of the primary branches; lateral branch.

*Size.*—Between 8.0 cm and 40 cm long (shorter at the upper nodes) and average 1.0 cm diameter at the base of branch.

*Stem.*—Rounded, glabrous, glaucous; average 85.0 cm tall and 3.0 cm diameter at base; stem color between RHS 184A and RHS 184B.

*Plant size.*—Unpinched plant with stems 85 cm tall; overall plant about 80 cm wide about 30 cm above the base (widest point).

*Internode.*—About 27 nodes per stem, average internode length about 3.0 cm of unpinched plant, varied between 2.0 to 6.0 cm widest in middle portion of stem.

Foliage description: Alternate; dentate; glabrous; heterophyllous; palmatifid, tri-lobed to cleft; with lobes open to less than 90 degrees, with some immature leaves oblong ovate with ovate to cordate bases and acute apexes; texture above lustrous in distal leaves and dull in proximal leaves, texture below dull; palmately veined; leaf blade size average 14 cm long and 12 cm wide, becoming smaller in distal portion of stem.

*Foliage color.*—Adaxial side nearest bright green between RHS 141B and RHS 141C with overlay of between RHS N187B and RHS N187A in light; abaxial side between RHS 138A and RHS 138B with tinting of nearest RHS 187A.

*Veins.*—Palmate; primary and secondary adaxial veins becoming reddish nearest RHS 185B; primary abaxial veins between RHS 187C near base and RHS 185B distally, secondary veins nearest RHS N186C.

*Petioles.*—Average size 6.5 cm long and 3.0 mm wide; mostly cylindrical with proximal petioles more plano-convex; glaucous, glabrous.

*Petiole color.*—Above between RHS 187C and RHS 187D in more light and where protected from light nearest RHS 139C; below between RHS 187A to RHS 185B in higher light and nearest RHS 182C where protected from light.

Flower description:

*Buds.*—One day prior to opening about 5.5 cm long and 3.5 cm in diameter, acute apex and bluntly rounded base, unopened petals wrinkled at veins, exposed petal color nearest RHS 187C; prior to showing petals: buds are about 3.5 cm long and 2.5 cm in diameter, ovoid with acute apex, carinate at the fusion seam of the sepals; color between RHS 141C and RHS 141D with veining, sepal carina and tinting between RHS N186C and RHS 187D.

*Epicalyx.*—Entire, smooth, glabrous, linear with sharply acute apex and attenuate base, curved around sepals; 11 to 12 per flower; about 2.5 cm long tapering to base of about 3.0 mm wide; adaxial and abaxial color between RHS 141C and RHS 143C except for the apical 4.0 to 6.0 mm between RHS 187C and RHS 187C.

*Sepals.*—Five, proximal half connate forming campanulate star-shaped calyx; acute apex; margin entire, edentate; about 4.0 cm long and 5.0 cm wide; abaxial color between RHS 141D and RHS 143C adaxial color between RHS 141D and RHS 143D; margins and five primary sepal veins tinted toward apex nearest between RHS 187C and RHS N186D.

*Flowers.*—Solitary, 16 to 22 per main stem without pinching; slightly cupped petals opening to about 160 degrees; upward and outwardly facing; average 20.0 cm across and 4.5 cm deep, larger in early part of flowering season; persist for a one to two days; effective for at least 12 weeks beginning mid July and lasting into October; no detectable fragrance.

*Petals.*—Five; glabrous, slightly lustrous, adnate to the androecium, imbricate to about 110% overlapping at widest part (petals completely overlapping the next petal and 10% of the petal in the position two over); shape: rounded; margins: entire, edentate; apex: rounded; base: short claw-like; size: average 12 cm long and 13 cm wide at widest portion (larger in earlier part of flowering season); center dark eye about 3.5 cm diameter.

*Petal color.*—Adaxial between RHS 60B and RHS 187C with a darker eye of nearest RHS 46A; abaxial color between RHS 60B and RHS 187C; petal veins ribbed on back and impressed on front producing a slightly ruffled appearance; vein color adaxial nearest RHS 187 on adaxial surface and the same as surrounding tissue on abaxial surface.

*Gynoecium.*—Style: enclosed in column about 7.5 cm long and 1.5 cm wide at base; column color nearest RHS 61C at base and RHS 60A distally; style protruding from column and split in distal 10.0 mm portion into five branches and protrudes from column, branch diameter 2.0 mm; branch color nearest RHS 59B; Stigma: five; globose, puberulose, about 3.0 mm in diameter, nearest RHS 59A; Ovary: superior, about 6.0 mm across at base and 6.0 mm tall; acute apex; color: closest to RHS 145B.

*Androecium.*—Filaments: numerous, about 140; less than 1.0 mm in diameter and about 6.0 mm long; attached to nearly the entire length of column; nearest RHS 60A; Anthers: reniform; about 2 mm long and 1 mm wide; nearest RHS 60D; Pollen: numerous, globose, less than 0.1 mm long, between RHS 22A and RHS 22B.

*Pedicel.*—Rounded, glabrous, from base of sepal to abscission point average 2.5 cm long and 3.0 mm wide on early flowers decreasing in distal flowers; color nearest RHS 183B with high light exposure and nearest RHS 138B with more shading.

*Peduncle.*—Rounded, glabrous, flowers are held easily visible on average 5.5 cm long from abscission point to stem and 3.0 mm wide, longer on earlier flowers; base color between RHS 144A and RHS 138A with a strong tinting of RHS 184B.

*Fruit.*—Few, loculicidal capsule; glabrous; globose, occasionally with abruptly acute apex; RHS N199B when mature.

*Seed.*—Minutely floccose, globose to slightly reniform; 3 to 4 mm in diameter; RHS 200A.

Disease resistance: Resistance beyond that of other hardy *hibiscus* cultivars has not been observed. The plant grows best with plenty of moisture and adequate drainage, but is able to tolerate some drought when mature. Hardiness at least from USDA zone 4 through 9, and other disease resistance is typical of that of other hardy *hibiscus* cultivars.

I claim:

1. A new cultivar of hardy herbaceous *Hibiscus* hybrid plant named 'Midnight Marvel' as herein illustrated and described, comprising a naturally-short, compact, heavy-branching rounded habit; also dark-green leaves with dark purple overlays and with a multitude of large, deep scarlet-red, slightly-cupped flowers over at least 12 weeks from early summer until frost suitable for potted plant culture, landscaping as a specimen or en masse, and especially suited for patios and confined spaces because of the compact habit.

* * * * *